US008148494B2

(12) United States Patent
Leonhartsberger et al.

(10) Patent No.: US 8,148,494 B2

(45) Date of Patent: Apr. 3, 2012

(54) SIGNAL PEPTIDE FOR THE PRODUCTION OF RECOMBINANT PROTEINS

(75) Inventors: Susanne Leonhartsberger, Jena (DE); Anton Candussio, Munich (DE); Gerhard Schmid, Gauting (DE)

(73) Assignee: Wacker Chemie AG, Munich (DE)

(*) Notice: Subject to any disclaimer, the term of this patent is extended or adjusted under 35 U.S.C. 154(b) by 286 days.

(21) Appl. No.: 11/859,257

(22) Filed: Sep. 21, 2007

(65) Prior Publication Data

US 2008/0076157 A1 Mar. 27, 2008

(30) Foreign Application Priority Data

Sep. 22, 2006 (DE) ......................... 10 2006 044 841

(51) Int. Cl.

*C07K 1/00* (2006.01)
*C07K 14/00* (2006.01)
*C07K 17/00* (2006.01)

(52) U.S. Cl. ........................................................ 530/350

(58) Field of Classification Search ................... 530/350

See application file for complete search history.

(56) References Cited

U.S. PATENT DOCUMENTS 5,395,927 A 3/1995 Böck et al.
6,514,730 B1 2/2003 Schmid et al.
7,455,987 B1 11/2008 Habermann

FOREIGN PATENT DOCUMENTS

EP 0 338 410 B1 9/1994
EP 0 448 093 B1 3/1996
EP 0 396 612 B1 7/1996
EP 0 677 109 B1 4/2000
JP 2003510041 A 3/2003
WO WO 01/21662 A 3/2001
WO WO 01/94418 A 12/2001

OTHER PUBLICATIONS

Zambonelli et al Enzyme and Microbial Technology 2003 vol. 33 pp. 676-688.*

U.S. Patent 6,514,730 B1 corresponding to EP 0 448 093 B1.

Patbase Abstract corresponding to EP 0 338 410 B1.

Skerra et al., A general vector, PASK84, for cloning, bacterial production, and single-step purification of antibody $F_{ab}$ fragments, GENE, 1994, pp. 79-84, v. 141.

Driessen et al., The Sec system, Cell Regulation, 1998, pp. 216-222.

Lee et al., Secretory Production of Therapeutic Proteins in *Escherichia coli,* Methods in Molecular Biology, V. 308, pp. 31-41, 2005.

Ray et al., Production of salmon calcitonin by direct expression of a glycine-extended precursor in *Escherichia coli,* Protein Expression & Purification, 2002, pp. 249-259.

Nagahari et al., Secretion into the culture medium of a foreign gene product from *Escherichia coli:* use of the *ompF* gene for secretion of human β-endorphin, The EMBO Journal, V. 4, n. 13A, pp. 3589-3592, 1985.

Yang et al., One Hundred Seventy-Fold Increase in Excretion of an FV Fragment-Tumor Necrosis Factor Alpha Protein (sFV/TNF-α) from *Escherichia coli* Caused by the Synergistic Effects of Glycine and Triton X-100, Applied and Environmental Microbiology, 1998, pp. 2869-2874, v. 64, n. 8.

Choi et al., Secretory and extraceullar production of recombinant proteins using *Escherichia coli,* Appl. Microbiol Biotechnol, v. 64, pp. 625-635, 2004.

Binder et al., Cyclodextrin-glycosyltransferase from *Klebsiella pneumoniae* M5al: cloning, nucleotide sequence and expression, Gene, 1986, excerpt from pp. 269-277.

* cited by examiner

*Primary Examiner* — Gary Nickol
*Assistant Examiner* — Nina Archie
(74) *Attorney, Agent, or Firm* — Brooks Kushman P.C.

(57) ABSTRACT

The present invention comprises a signal peptide with a cleavage site to a recombinant protein, wherein the last three amino acids before the cleavage site are alanine-phenylalanine-alanine (AFA).

3 Claims, 5 Drawing Sheets

Fig. 1: Overview of amino acids, grouped by their biochemical properties
amino acids with hydrophobic residues
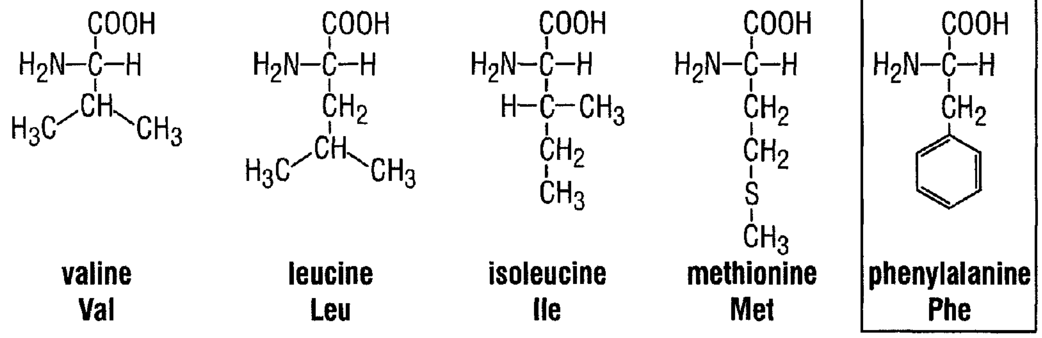
amino acids with hydrophilic residues
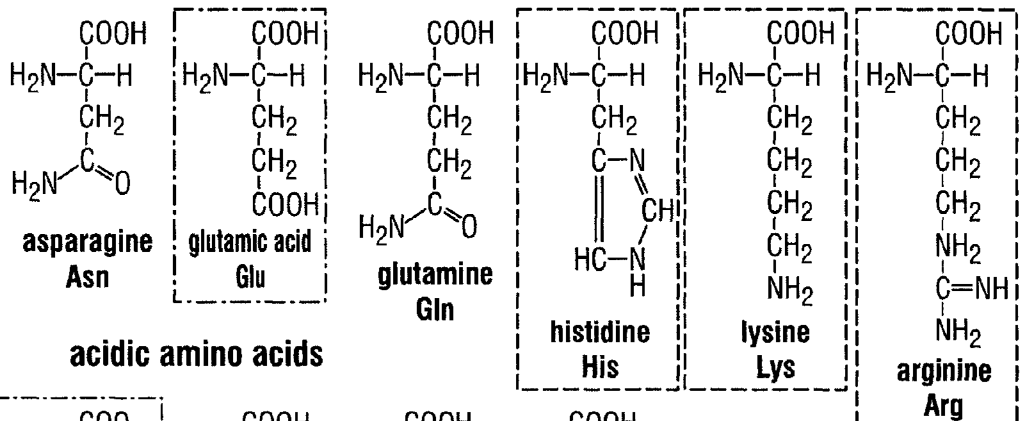
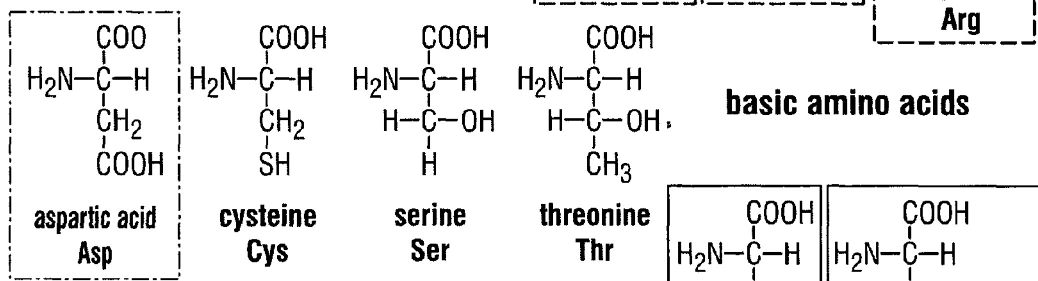
neutral amino acids
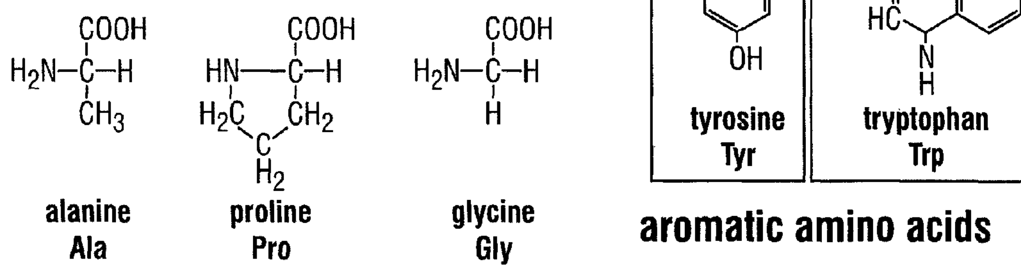
aromatic amino acids

Fig. 2: Plasmid pJF118ut.
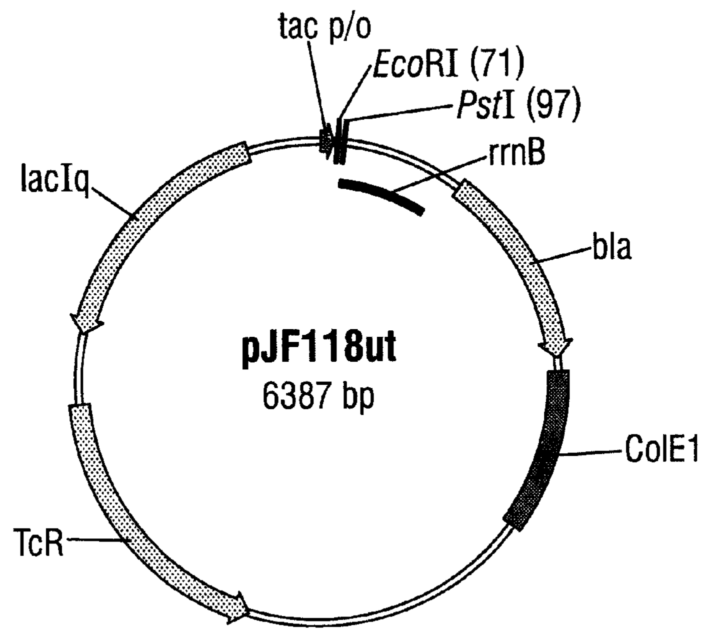
Fig. 3: Plasmid pCGT.
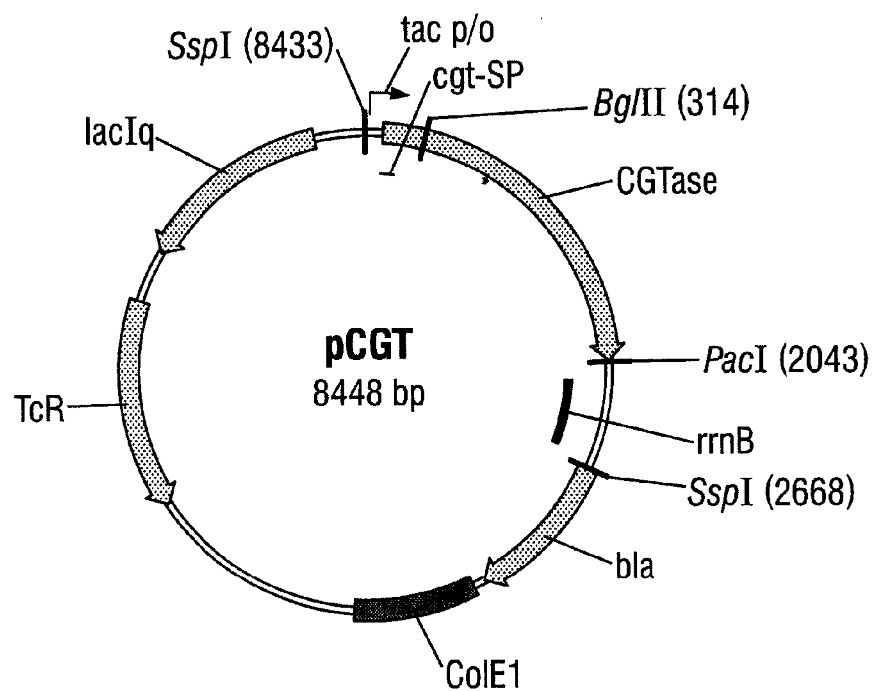

Fig. 4: Plasmid pKP651.
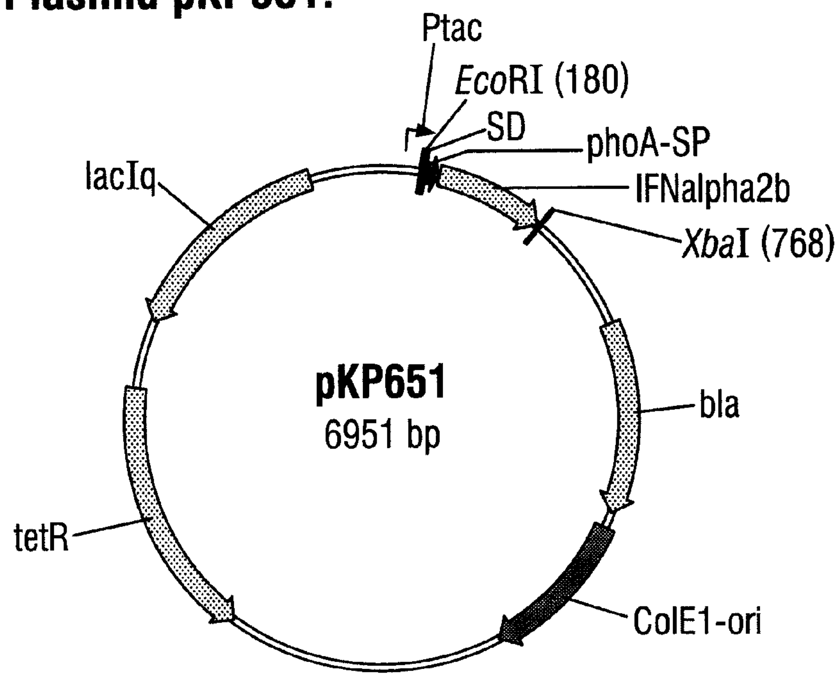
Fig. 5: Plasmid pKP652.
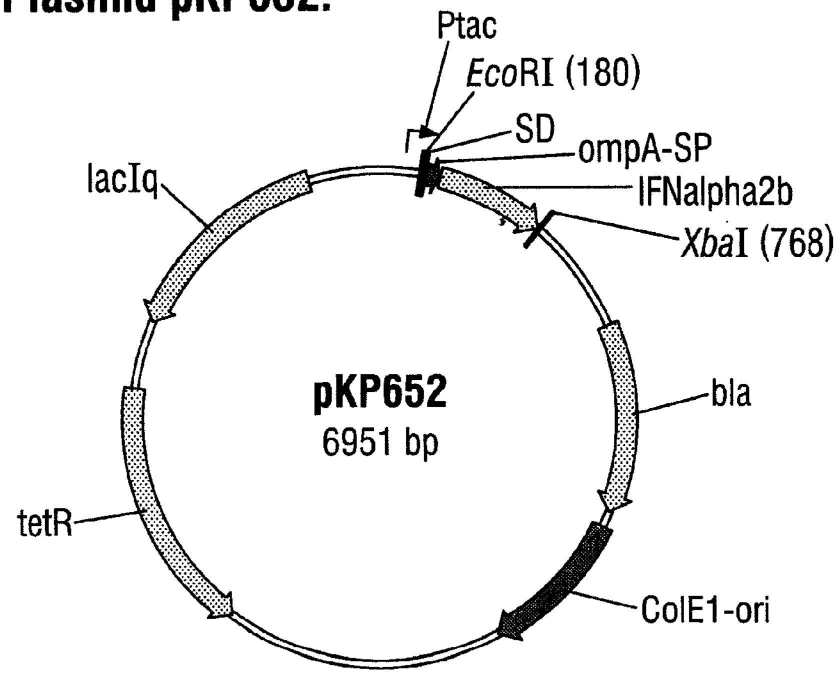

Fig. 6: Plasmid pKPIFN.
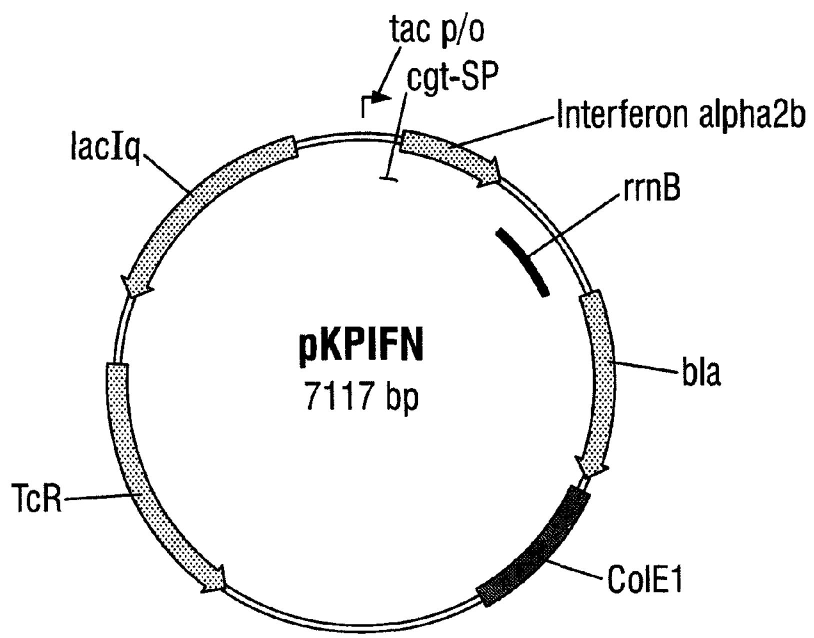
Fig. 7: Plasmid pBaBIFN1.
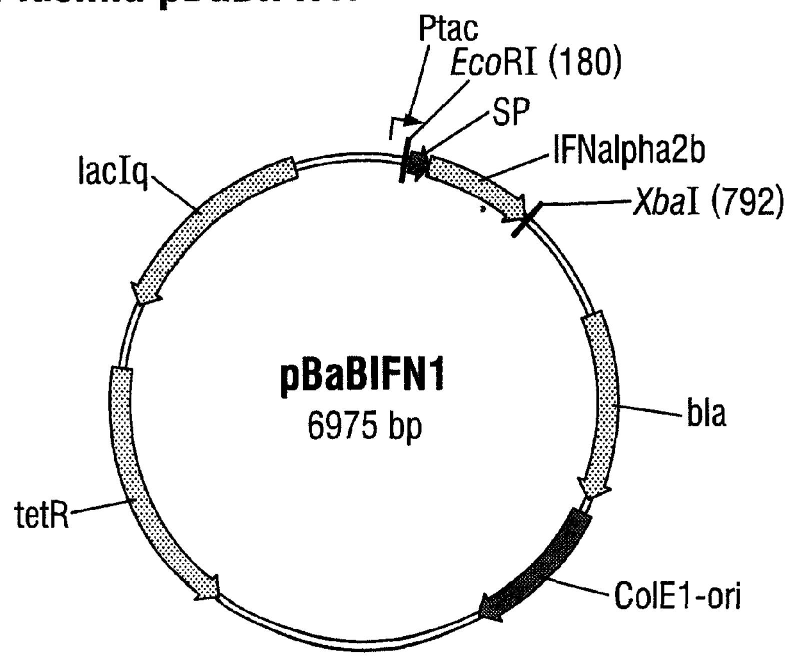

Fig. 8: Plasmid pFab-anti-lysozyme.
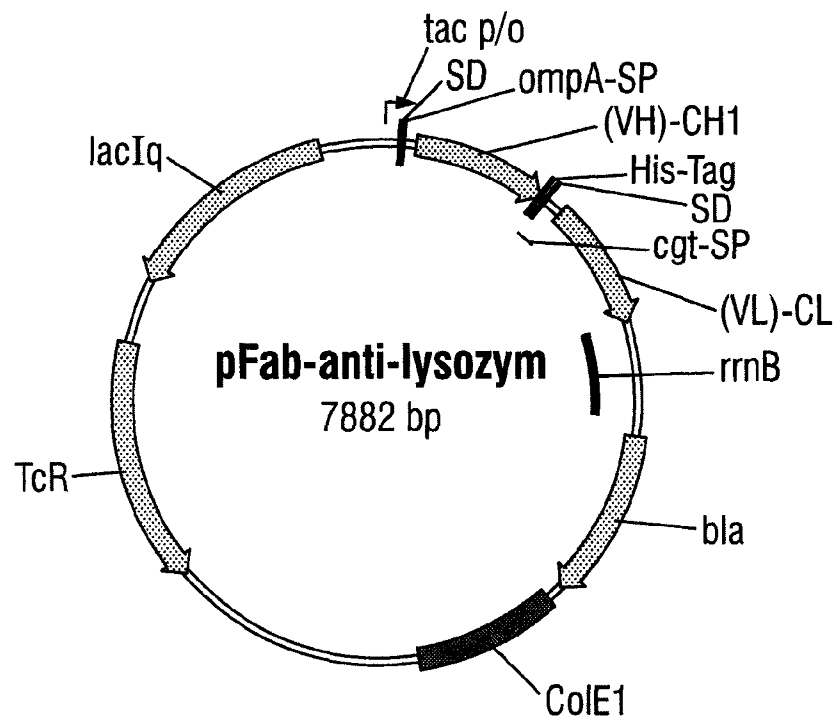
Fig. 9: Increased interferon α2b production on use of the signal sequence according to the invention (Ex. 2).
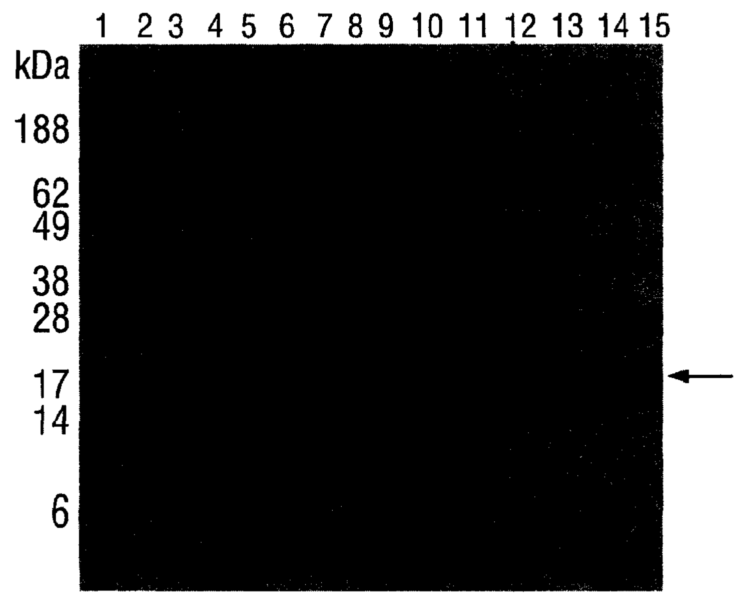

SIGNAL PEPTIDE FOR THE PRODUCTION OF RECOMBINANT PROTEINS

SEQUENCE LISTING

The text file Sequence 904ST25.txt, created Sep. 21, 2007, and of size 13 kilobytes, filed herewith, is hereby incorporated by reference.

BACKGROUND OF THE INVENTION

1. Field of the Invention

The invention relates to a signal peptide for the production of recombinant proteins.

2. Background Art

The large-scale industrial production of recombinant proteins is of increasing importance to the biotechnology and pharmaceutical industry. In general, recombinant proteins are produced either in mammalian cell culture or in microbial systems. Compared to mammalian cell culture, microbial systems have the advantage that in this manner recombinant proteins can be produced in a shorter time and with lower costs. Hence bacteria, preferably those of the genus *Escherichia*, more preferably *E. coli*, are most suitable for the production of recombinant proteins. In *E. coli*, recombinant proteins can in principle be produced in various ways:

1. Intracellular production as soluble protein;
2. Intracellular production as inclusion bodies;
3. Secretion into the periplasm or into the nutrient medium.

The production process for the recombinant protein always consists of two parts. The first part is the fermentation, which leads to the crude product. In this case, the fermentation result, which contains the recombinant protein and also contaminating host proteins, is described as the crude product. The second part of the production process comprises the purification of the recombinant protein starting from the crude product.

In addition to the production costs of the crude product which is present directly after the fermentation as a mixture containing the recombinant protein and host proteins, the labor and costs for the production of the recombinant protein are also to a considerable extent determined by the costs of purification of the crude product to the desired recombinant protein. The purification is in most cases performed over several stages by means of chromatographic procedures. Purification from contaminating host proteins, some of which are immunogenic or toxic, is an important aspect.

The secretion of proteins in *E. coli* in most cases takes place via the so-called sec pathway (Driessen et al., 1998). This system is responsible for the export of certain bacterial proteins. The genes for these proteins each have a so-called signal sequence at the 5' end. During protein synthesis, this is translated into a signal peptide and effects the secretion of the protein through the cytoplasmic membrane. After secretion, the signal peptide is removed by the enzyme signal peptidase and the mature protein is released.

The sec system can also be used for the secretion of recombinant, for example heterologous, proteins (Lee et al., Methods in Molecular Biology 308, 2005). For this, the recombinant gene for the recombinant protein to be produced is linked with a signal sequence ("in-frame fusion"), which results in the production of a signal peptide-protein fusion product. The signal peptide encoded by the signal sequence mediates the secretion of the recombinant protein across the cytoplasmic membrane into the periplasm by means of the bacterial sec system. In this, the signal peptide is cleaved off at the cleavage site between signal peptide and the recombinant protein, and the desired recombinant protein is obtained in the periplasm. The recombinant protein can then be purified from the periplasm.

Compared to the other production processes, secretion offers the advantage that the recombinant protein is obtained directly as native, soluble, correctly folded protein, which in contrast to the "inclusion body" process does not have to be denatured and again renatured, a step which is attended by major losses in yield. Moreover, in this case the crude product is contaminated with fewer host proteins compared to intracellular soluble production, since the periplasm of bacteria contains far fewer host proteins than the cytoplasm.

Under certain conditions or in certain bacterial strains, the recombinant protein is released from the periplasm into the nutrient medium (e.g. Ray et al., 2002; EP0338410B1; Nagahari et al., 1985; Yang et al., 1998; EP0677109B1) and can be purified from this.

Compared to secretion into the periplasm, secretion of the proteins into the nutrient medium offers an advantage that the protein is then present in still purer form. Moreover as the first purification step, laborious preparation of the periplasm or disintegration of the cells is unnecessary, but rather the much simpler and more reproducible removal of the whole cells.

As aforesaid, for the secretion of a protein to be produced, the gene coding for it is linked with a signal sequence, which has the effect that the protein to be produced is initially produced as a fusion product with the signal peptide encoded by the signal sequence. This signal peptide effects the secretion of the protein produced.

Signal peptides are made up of three regions: the N-terminal N region (1-5 amino acids) as a rule contains one or more amino acids, which bear a positive charge. The H region lying in the middle mostly consists of 7-15 amino acids, many of which are hydrophobic. The C region as a rule comprising 3-7 amino acids mostly contains neutral, short-chain amino acids (A, G, S, T or C) at position −1 and −3 before the cleavage site.

Various signal sequences and the corresponding signal peptides are described in the state of the art, e.g. phoA, ompA, pelB, ompF, ompT, lamB, malE, staphylococcal protein A and stII (Choi & Lee, 2004; EP0396612B1). The signal peptide of the cyclodextrin glycosyltransferase (CGTase) from various strains, such as for example *Klebsiella oxytoca* (*Klebsiella pneumoniae* M5a1), and the use thereof for the secretion of CGTase in *E. coli* strains is described in U.S. Pat. No. 5,395,927. Also described (EP0448093B1) is the fact that a recombinant protein, such as for example a hirudin derivative, can be produced and secreted in *E. coli* strains through fusion of the gene for the recombinant protein with the signal sequence of the CGTase. In the case of a specific hirudin derivative, this leads to a yield of 250 mg/l in a shaker flask culture and 2.63 g/l in a fermentation. EP0448093B1 however also describes the fact that with another recombinant protein yields of only up to 25 mg/l were obtained. The signal peptide of CGTase is like all other known signal peptides—not capable of mediating secretion of any recombinant protein in equally high yields. Since every recombinant protein is encoded by its own DNA sequence and in particular the DNA sequence at the transition point between signal sequence and the sequence coding for the recombinant protein is therefore different, as a rule an optimal signal peptide must be found for each recombinant protein.

SUMMARY OF THE INVENTION

One objective of the present invention is to provide novel signal peptides. The problem is solved by means of a signal peptide, which is characterized in that its last three amino acids before the cleavage site are alanine-phenylalanine-alanine (AFA).

BRIEF DESCRIPTION OF THE DRAWINGS

FIG. 1 shows an overview of amino acids.

FIG. 2 shows the plasmid map of plasmid pJF118ut.

FIG. 3 shows the plasmid map of plasmid pCGT.

FIG. 4 shows the plasmid map of plasmid pKP651.

FIG. 5 shows the plasmid map of plasmid pKP652.

FIG. 6 shows the plasmid map of plasmid pKPIFN.

FIG. 7 shows the plasmid map of plasmid pBaBIFN1.

FIG. 8 shows the plasmid map of plasmid pFab-anti-lysozyme.

FIG. 9 shows an immunoblot wherein culture supernatants from interferon•2b-producing cells (see Example 2) are analyzed.

Track 1: Size standard;

Tracks 2 and 3: 20 and 40 ng interferon•2b;

Tracks 4-6: Supernatant from cultures with plasmid pBaB-IFN1 after 24, 48 and 72 hrs;

Tracks 7-9: Supernatant from cultures with plasmid pKPIFN after 24, 48 and 72 hrs;

Tracks 10-12: Supernatant from cultures with plasmid pKP651 after 24, 48 and 72 hrs;

Tracks 13-15: Supernatant from cultures with plasmid pKP652 after 24, 48 and 72 hrs.

In each case, 5 μl were applied at 24 hrs, and 1 μl at 48 hrs and 72 hrs.

DETAILED DESCRIPTION OF THE PREFERRED EMBODIMENT(S)

In an embodiment of the present invention, a signal peptide in which the last three amino acids before the cleavage site are alanine-phenylalanine-alanine (AFA) is provided. Preferably, the signal peptide has the amino acid sequence: MKRNRFFNTSAAIAISIALQIFFPSASAFA (SEQ ID NO: 1) or an amino acid sequence wherein compared to SEQ ID NO: 1 one to ten preferably one to five and more preferably one to three amino acids, with the exception of the last three amino acids before the cleavage site, are altered.

As set forth above, a signal peptide consists of different regions, which contain amino acids from a certain group (e.g. charged or hydrophobic or short-chain). The person skilled in the art can therefore create a novel signal peptide with unchanged properties by replacement of an amino acid by another with comparable properties. For this reason, signal peptides wherein, compared to SEQ ID NO: 2, 1-10, more preferably 1-5, most preferably 1-3 amino acids, are altered, should also be regarded as signal peptides according to the invention. Preferably these are exchanges of amino acids that have similar biochemical properties, for example basic amino acids (lysine, arginine, histidine) for basic ones, and acidic amino acids (aspartate, glutamate, asparagine, glutamine) for acidic ones, hydrophobic for hydrophobic, etc. An overview of the biochemical properties of amino acids is shown in FIG. 1.

The invention further relates to the signal sequence coding for the signal peptide according to the invention. This is characterized in that it codes for a signal peptide with a cleavage site whereof the last three amino acids before the cleavage site are alanine-phenylalanine-alanine. Preferably this is a signal sequence with the DNA sequence ATGAAAAGAAACCGTTTTTTTAATACCTCGGCTGCTATTGCCATTTCGATTGCATTACAGAT CTTTTTTCCGTCCGCTTCCGCTTTCGCT (SEQ ID NO: 2) and all DNA sequences, which, on the basis of the degenerate genetic code, code for the amino acid sequence SEQ ID NO: 1.

During a screening operation, the properties of various signal sequences, which had been obtained by modification of the CGTase signal sequence (MKRNRFFNTSAAIAISIALNTFFCSMQTIA, SEQ ID NO: 3) were compared. Surprisingly, it was found that the signal sequence according to the invention is suitable for the production and secretion of a larger spectrum of recombinant proteins in higher yield in host cells than the CGTase signal sequence or also other signal sequences.

A DNA sequence according to the invention can be obtained by gene synthesis or ligation of appropriate oligonucleotides by methods known to the person skilled in the art. The DNA sequence according to the invention is linked in-frame to the gene of the recombinant protein to be produced by methods known to the person skilled in the art (e.g. after Lee et al., 2005) and can be introduced into a vector.

This combination of signal sequence and recombinant gene is preferably equipped with expression signals (promoter, transcription and translation start, ribosome binding site) functional in *E. coli*. All promoters known to the person skilled in the art, on the one hand for example inducible promoters, such as the lac, tac, trc, lambda PL, ara or tet promoter or sequences derived therefrom are suitable as promoters. On the other hand, constitutive expression can also be effected through the use of a constitutive promoter, such as for example the GAPDH promoter. However, the promoter normally linked with the gene of the recombinant protein to be produced can also be used.

Accordingly, the invention also relates to an expression construct comprising an expression signal, a signal sequence according to the invention and an in-frame linked recombinant gene coding for a recombinant protein which is to be produced.

The expression construct according to the invention is introduced into a host cell by the use of methods known to the person skilled in the art. This is effected for example in a vector, such as a plasmid, that is a derivative of a known expression vector such as pUC18, pBR322, pACYC184, pASK-IBA3 or pET. For example, genes that code for resistance to ampicillin, tetracycline, chloramphenicol, kanamycin or other antibiotics are suitable as selection markers for plasmids.

Plasmids that contain the signal sequence according to the invention or an expression construct according to the invention are also an object of the invention. The recombinant protein is preferably a heterologous protein. Preferably the recombinant protein is a protein, which is used in technical preparations, or a protein, which is used as a pharmaceutical active substance (biologics or biopharmaceutical). Examples of such proteins are hirudin, insulin, interferons, such as alpha or beta interferon (e.g. interferon α2b), antibodies or antibody fragments (such as for example Fab fragments, scFv) or other binding proteins or enzymes, such as CGTase.

The expression construct according to the invention is introduced into a microorganism cell (host cell) by methods known to the person skilled in the art. Subsequently, the expression construct according to the invention can be present in the host cell as a plasmid or be integrated into the chromosome of the host cell.

Another object includes microbes that contain the signal sequence according to the invention or an expression construct according to the invention or a plasmid according to the invention.

The host cells are cells of a bacterial strain from the family Enterobacteriaceae, preferably a strain of the species *Escherichia coli*. More preferable is an *Escherichia* (*E.*) *coli* strain, which is characterized in that after transformation with the expression construct according to the invention it has a higher concentration of the recombinant protein in the periplasm or in the nutrient medium than the strain *E. coli* W3110 (ATCC 27325) after transformation with the expression construct according to the invention.

The following *E. coli* strains are most preferable:

BLR: Ray et al., 2002, commercially available from Novagen

K802=CGSC* 5610: Yang et al., 1998

WCM105: preparable according to EP0338410B1

MM28=CGSC* #5892: Nagahari et al., 1985

RV308=ATCC** 31608; EP0677109B1

RR1: ATCC** 31434: Nagahari et al., 1985

* commercially available via the *E. coli* Genetic Stock Center CGSC (830 Kline Biology Tower, MCD Biology Department, 266 Whitney Ave., PO box 208103, Yale University, New Haven,

** commercially available via LGC Promochem, Mercatorstr. 51, 46485 Wesel, Germany.

The secretion of the protein produced takes place via the sec system of the host cell. After secretion into the periplasm, the signal peptide according to the invention is removed by a signal peptidase (e.g. LepB in *E. coli*) and the desired recombinant protein is formed.

The invention thus also relates to a process for the fermentative production of a recombinant protein by means of a host cell containing the expression construct according to the invention in a fermentation medium. This process is characterized in that a host strain according to the invention is cultured in a fermentation medium, the host strain produces the recombinant protein in the form of in-frame signal peptide-protein fusion product, wherein the signal peptide is a signal peptide according to the invention and on secretion of signal peptide-protein fusion product through the cytoplasmic membrane into the periplasm, the signal peptide is cleaved off at the cleavage site between signal peptide and the recombinant protein and the desired recombinant protein is obtained in the periplasm or the fermentation medium and the recombinant protein is purified after the fermentation.

The recombinant protein is secreted into the periplasm or preferably into the fermentation medium in fermentation. Moreover, the recombinant protein can be purified either from the periplasm of the host cells or preferably from the fermentation medium after removal of the cells.

The fermentation of the bacterial strain for the production of the recombinant protein according to the invention is preferably effected in a whole medium or minimal salt medium. These media are known from the literature.

As the carbon source, in principle all utilizable sugars, sugar alcohols, organic acids or salts thereof, starch hydrolyzates, molasses or other substances can be used. However, glucose or glycerin is preferably used. Combined feeding with several different carbon sources is also possible. As nitrogen sources, urea, ammonia and salts thereof, nitrate sources and other N sources can be used. The possible nitrogen sources also include complex amino acid mixtures, such as yeast extract, peptone, malt extract, soya peptone, casamino acids, corn steep liquor, and NZ amines (e.g. Kerry Bio-Science, Chicago, USA).

Furthermore, other components, such as vitamins, salts, yeast extract, amino acids and trace elements, through which cell growth is improved, can be added to the medium.

The strain is preferably incubated under aerobic culturing conditions for a period of 16-150 hrs and in the region of the optimal growth temperature for the strain in question.

As the optimal temperature region, 15-55° C. is preferred. A temperature between 28 and 37° C. is more preferable.

The strain can be grown in a shaker flask or fermenter, there being no restrictions as regards volume. It can be grown in a batch process, a fed batch or a continuous process.

Expression of the recombinant protein takes place either constitutively, i.e. non-induced, or by induction by physical or physiological stimuli. Expression can for example be induced by addition of a substance inducing the promoter, for example lactose or IPTG in the case of lac or tac promoter.

The purification of proteins from the periplasm or the culture medium can be effected by methods known to the person skilled in the art, such as disintegration or removal of the cells, chromatographic purification, complexation, filtration or precipitation of the protein.

The cells contain interferon•2b expression plasmids, which differ in their signal sequences. The interferon•2b formed was detected with antibodies (arrow). The use of the signal sequence according to the invention results in increased interferon•2b production.

The following examples serve for further illustration of the invention.

Example 1: Creation of a Signal Sequence According to the Invention and a Vector According to the Invention As the starting plasmid, the plasmid pCGT was created as follows:

A DNA fragment with the SEQ ID NO: 4, which contains a cyclodextrin glycosyltransferase (CGTase) gene from *Klebsiella pneumoniae* M5a1 (Gene bank No. M15264), was prepared by gene synthesis. This DNA fragment was cloned into the expression vector pJF118ut (FIG. 2), which has been deposited at the DSMZ —Deutsche Sammlung von Mikroorganismen und Zellkulturen GmbH [German Collection of Microorganisms and Cell Cultures](Braunschweig) under the number DSM 18596. pJF118ut is a derivative of the known expression vector pKK223-3 (Amersham Pharmacia Biotech) and in addition to the β-lactamase gene and the tetracycline resistance gene also contains the tac promoter, which is repressed by the LacIq gene product, the gene whereof is also present on the plasmid, and which can be switched on by an inducer, such as for example D-lactose or isopropyl-β-D-thiogalactopyranoside (IPTG).

The plasmid pJF118ut was completely cleaved with the restriction enzyme EcoRI and the bases remaining at each of the 5' ends of the linear DNA fragment were removed with S1 nuclease. The vector DNA molecule prepared in this manner was ligated with the CGTase-containing DNA fragment (SEQ ID NO: 4) using T4 ligase. The strain DH5α was transformed with the ligation preparation by the $CaCl_2$ method, selection for plasmid-containing cells being performed using ampicillin (100 mg/l). The plasmid was isolated again from ampicillin -resistant transformants and examined by restriction analysis. The plasmid created in this manner, wherein the expression of the CGTase gene is under the control of the tac promoter, was designated pCGT (FIG. 3).

The gene for a CGTase fused to the signal sequence for the CGTase was removed: for this, the 8448 bp plasmid was cleaved with the restriction enzymes SspI and PacI in a partial digestion by methods known to the person skilled in the art. The 6390 bp fragment was isolated and treated with Klenow enzyme, whereby the ends were smoothed. The 2058 bp fragment was removed.

Subsequently, the following four DNA fragments were prepared by gene synthesis:

phoA-IFN·2b

SEQ ID NO: 5

ATTCTGAAATGAGCTGTTGACAATTAATCATCGGCTCGTATAATGTGTGG
AATTGTGAGCGGATAACAATTTCACACAGGAAACAGAATTCTAAGGAGGA
AATTATATGAAACAAAGCACTATTGCACTGGCACTCTTACCGTTACTGTT
TACCCCTGTGACAAAAGCTTGTGACTTACCTCAGACCCATTCACTGGGCT
CACGCCGTACGCTGATGCTGTTAGCACAGATGCGTCGCATTTCTCTGTTT
AGTTGTTTGAAAGACCGTCATGATTTTGGGTTCCCGCAAGAAGAGTTTGG
TAATCAGTTTCAGAAAGCCGAAACTATTCCGGTTCTGCACGAAATGATTC
AACAGATTTTTAACCTGTTTTCGACAAAGGATAGCTCTGCCGCGTGGGAT
GAAACCTTACTGGATAAGTTCTACACCGAACTGTACCAGCAACTGAATGA
TCTGGAAGCATGCGTTATCCAGGGCGTGGGTGTCACAGAAACTCCGCTGA
TGAAGGAGGACAGCATTCTGGCGGTGCGCAAATATTTCCAGCGTATCACG
CTGTATCTGAAAGAGAAAAAATATTCGCCATGCGCGTGGGAGGTCGTGCG
CGCGGAGATCATGCGCAGTTTCTCTTTGAGCACCAACCTGCAAGAATCCT
TGCGTTCCAAAGAATAATAGTCTAGAAGCTTGGCTGTTTTGGCGGATGAG ompA-IFN·2b

SEQ ID NO: 6

ATTCTGAAATGAGCTGTTGACAATTAATCATCGGCTCGTATAATGTGTGG
AATTGTGAGCGGATAACAATTTCACACAGGAAACAGAATTCTAAGGAGGA
AATTATATGAAAAAGACAGCTATCGCGATTGCAGTGGCACTGGCTGGTTT
CGCTACCGTAGCGCAGGCTTGTGACTTACCTCAGACCCATTCACTGGGCT
CACGCCGTACGCTGATGCTGTTAGCACAGATGCGTCGCATTTCTCTGTTT
AGTTGTTTGAAAGACCGTCATGATTTTGGGTTCCCGCAAGAAGAGTTTGG
TAATCAGTTTCAGAAAGCCGAAACTATTCCGGTTCTGCACGAAATGATTC
AACAGATTTTTAACCTGTTTTCGACAAAGGATAGCTCTGCCGCGTGGGAT
GAAACCTTACTGGATAAGTTCTACACCGAACTGTACCAGCAACTGAATGA
TCTGGAAGCATGCGTTATCCAGGGCGTGGGTGTCACAGAAACTCCGCTGA
TGAAGGAGGACAGCATTCTGGCGGTGCGCAAATATTTCCAGCGTATCACG
CTGTATCTGAAAGAGAAAAAATATTCGCCATGCGCGTGGGAGGTCGTGCG
CGCGGAGATCATGCGCAGTTTCTCTTTGAGCACCAACCTGCAAGAATCCT
TGCGTTCCAAAGAATAATAGTCTAGAAGCTTGGCTGTTTTGGCGGATGAG cgt-IFN·2b

SEQ ID NO: 7

ATTCTGAAATGAGCTGTTGACAATTAATCATCGGCTCGTATAATGTGTGG
AATTGTGAGCGGATAACAATTTCACACAGGAAACAGAATTCTAAGGAGGA
AATTATATGAAAAGAAACCGTTTTTTTAATACCTCGGCTGCTATTGCCAT
TTCGATTGCATTAAATACTTTTTTTTGTAGCATGCAGACGATTGCTTGTG
ACTTACCTCAGACCCATTCACTGGGCTCACGCCGTACGCTGATGCTGTTA
GCACAGATGCGTCGCATTTCTCTGTTTAGTTGTTTGAAAGACCGTCATGA
TTTTGGGTTCCCGCAAGAAGAGTTTGGTAATCAGTTTCAGAAAGCCGAAA
CTATTCCGGTTCTGCACGAAATGATTCAACAGATTTTTAACCTGTTTTCG

-continued

ACAAAGGATAGCTCTGCCGCGTGGGATGAAACCTTACTGGATAAGTTCTA
CACCGAACTGTACCAGCAACTGAATGATCTGGAAGCATGCGTTATCCAGG
GCGTGGGTGTCACAGAAACTCCGCTGATGAAGGAGGACAGCATTCTGGCG
GTGCGCAAATATTTCCAGCGTATCACGCTGTATCTGAAAGAGAAAAAATA
TTCGCCATGCGCGTGGGAGGTCGTGCGCGCGGAGATCATGCGCAGTTTCT
CTTTGAGCACCAACCTGCAAGAATCCTTGCGTTCCAAAGAATAATAGTCT
AGAAGCTTGGCTGTTTTGGCGGATGAG

AFA-IFN·2b

SEQ ID NO: 8

ATTCTGAAATGAGCTGTTGACAATTAATCATCGGCTCGTATAATGTGTGG
AATTGTGAGCGGATAACAATTTCACACAGGAAACAGAATTCTAAGGAGGA
AATTATATGAAAAGAAACCGTTTTTTTAATACCTCGGCTGCTATTGCCAT
TTCGATTGCATTACAGATCTTTTTTCCGTCCGCTTCCGCTTTCGCTTGTG
ACTTACCTCAGACCCATTCACTGGGCTCACGCCGTACGCTGATGCTGTTA
GCACAGATGCGTCGCATTTCTCTGTTTAGTTGTTTGAAAGACCGTCATGA
TTTTGGGTTCCCGCAAGAAGAGTTTGGTAATCAGTTTCAGAAAGCCGAAA
CTATTCCGGTTCTGCACGAAATGATTCAACAGATTTTTAACCTGTTTTCG
ACAAAGGATAGCTCTGCCGCGTGGGATGAAACCTTACTGGATACGTTCTA
CACCGAACTGTACCAGCAACTGAATGATCTGGAAGCATGCGTTATCCAGG
GCGTGGGTGTCACAGAAACTCCGCTGATGAAGGAGGACAGCATTCTGGCG
GTGCGCAAATATTTCCAGCGTATCACGCTGTATCTGAAAGAGAAAAAATA
TTCGCCATGCGCGTGGGAGGTCGTGCGCGCGGAGATCATGCGCAGTTTCT
CTTTGAGCACCAACCTGCAAGAATCCTTGCGTTCCAAAGAATAATAGTCT
AGAAGCTTGGCTGTTTTGGCGGATGAG

All the DNA fragments contain the tac promoter region and the gene for interferon•2b and four different signal sequences (shown bold). These four different signal sequences code for the following four different signal peptides, the first three signal peptides (SEQ ID NO: 9, 10, 3) being known from the state of the art, and the fourth signal peptide (SEQ ID NO: 2) being according to the invention:

phoA:
MKQSTIALALLPLLFTPVTKA SEQ ID NO: 9 ompA:
MKKTAIAIAVALAGFATVAQA SEQ ID NO: 10 cgt:
MKRNRFFNTSAAIAISIALNTFFCSMQTIA SEQ ID NO: 3

AFA:
MKRNRFFNTSAAIAISIALQIFFPSASAFA SEQ ID NO: 2

Through these cloning operations, the following four plasmids were formed:

- pKP651 (phoA signal sequence) FIG. 4
- pKP652 (ompA signal sequence) FIG. 5
- pKPIFN (cgt signal sequence) FIG. 6
- pBaBIFN1 (AFA: signal sequence according to invention) FIG. 7

These plasmids were introduced by known methods into the *E. coli* strain DH5α. The strain according to the invention DH5/pBaBIFN1 has been deposited at the DSMZ (Deutsche Sammlung von Mikroorganismen und Zellkulturen GmbH, D-38142 Braunschweig [German Collection of Microorganisms and Cell Cultures]) under the number DSM 18343 in accordance with the Budapest Treaty.

Example 2: Increasing Interferon Production by Use of the Signal Sequence According to the Invention Plasmid pKP651 (phoA signal sequence), pKP652 (ompA signal sequence), pKPIFN (cgt signal sequence) and pBaBIFN1 (AFA signal sequence according to the invention)(see Example 1) were introduced into strain WCM105 (preparable according to EP0338410B1) by transformation by standard methods (by $CaCl_2$ transformation). Plasmid-containing strains were selected using ampicillin (100 mg/L).

The following strains were obtained:

WCM105/pKP651 (phoA signal sequence)

WCM105/pKP652 (ompA signal sequence)

WCM105/pKPIFN (cgt signal sequence)

WCM105/pBaBIFN1 (AFA signal sequence)

The production of interferon•2b in the resulting strains was studied. For this, the strains were cultured in 10 ml of LB medium containing 100 mg/L of ampicillin and with 1% glucose at 30° C. At an optical density of 0.5 at 600 nm (OD600), the production of interferon•2b was induced by addition of IPTG (isopropylthiogalactoside) to 0.5 mM. After 24 hrs, 48 hrs and 72 hrs, the interferon formed and secreted was quantified in the culture supernatant by separation of the proteins in the SDS gel and detection in the immunoblot with anti-interferon specific antibodies as follows:

1 μl (48 and 72 h) or 5 μl (24 h) of supernatant respectively were treated with sample buffer (2×Tris SDS -sample buffer (Invitrogen Cat. No. LC2676): 0.125 M Tris.HCl, pH 6.8, 4% w/v SDS, 20% v/v glycerin, 0.005% v/v bromophenol blue, 5% beta-mercaptoethanol). In addition, defined quantities of interferon•2b were applied as the standard. Denaturing of the proteins was effected by heating at 100° C. for 5 mins, cooling for 2 mins on ice and centrifuging down. The proteins were separated by electrophoresis in a 12% NuPAGE® Bis-Tris gel (Invitrogen Cat. No. NP0341) with 1×MES-containing running buffer (Invitrogen Cat. No. NP0002) (Electrophoresis parameters: 40 mins at 200 V).

Detection and quantification by immunoblot was carried out according to the following procedure:

Transfer in the wet blot procedure:

Module: Amersham: Hoefer TE 22 Mini Tank Transfer Unit, Code Number: 80-6204-26

Membrane: nitrocellulose membrane (Schleicher & Schuell, BA 85, cellulose nitrate (E), 0.45 μm pore size)

Cut Whatman filters and nitrocellulose membrane to suitable size and soak in transfer buffer (Invitrogen Cat. No. LC3675) in the absence of air bubbles using foamed material pieces (sponges).

Structure of sandwich: black grating, connection with the cathode, 2 sponges, each 3 mm thick, Whatman paper, SDS-polyacrylamide gel, NC membrane, Whatman, 1 sponge, 6 mm thick, white grating, connection with the anode.

Transfer conditions: I=200 mA constant current, U=unlimited, run time 60 mins.

Prehybridization

Incubation of the membrane in 25 ml of prehybridization buffer. Rock for 30 mins at RT.

Hybridization—1st antibody

Incubation of the membrane in 25 ml of prehybridization buffer+0.15 μg/ml (->3.75 μg) anti-human-IFN alpha antibody (Pepro Tech EC, via Biozol Cat. No.: 500-P32A)

Rock for 90 mins or overnight at RT.

Washing

Rock for 10 seconds with 1×PBS, RT, pour off buffer

Rock for 2×15 mins with 1×PBS, RT, pour off buffer

Hybridization—2nd antibody

Incubation of the membrane in 25 ml of prehybridization buffer+25 μl (1:1000) goat anti-rabbit IgG horseradish peroxidase conjugate (HRP) (Southern Biotech, via Biozol Cat. No.: 4050-05)

Rock for 60 mins at RT.

Washing

Rock for 10 seconds with 1×PBS, RT, pour off buffer

Rock for 2×15 mins with 1×PBS, RT, pour off buffer

Detection by chemiluminescence

Prepare Lumi-Light Western blotting substrate (Roche, Cat. No.: 2015200): mix Lumi-Light luminol/enhancer solution and Lumi-Light stable peroxide solution in the ratio 1:1:3 ml/NC membrane.

Incubate blot for 5 mins at RT with Lumi-Light Western blotting substrate, allow excess to run off, cover membrane with clingfilm and immediately cover with an X-ray film (Kodak, X-OMAT), expose for 2 mins, develop and fix. For weak signals, the exposure is repeated over a longer time period.

Buffers

Prehybridization buffer: 5% skim milk powder in 1×PBS

10×PBS: 100 mM $NaH_2PO_4$, 1.5 M NaCl, pH 7.5 with NaOH, 0.5% Triton 100

1×PBS: dilute 10×PBS 1:10 with completely desalinated water

Quantification

A quantitative assessment was made after scanning in the immunoblots with a Biorad GS-800 calibrated densitometer using the Quantity One 1-D-Analysis Software (Biorad) by comparison with the standard applied.

FIG. 9 shows an immunoblot from this example. In Table 1, the quantified yields of interferon•2b are summarized:

TABLE 1

Yields of interferon•2b obtained after 24, 48 or 72 hrs with different plasmids, which each differ by the signal sequence used.

| Plasmid | Signal sequence | Culture (hrs) | Yield of interferon•2b (mg/l) |
|---|---|---|---|
| pBaBIFN1 | AFA | 24 | 4 |
| pBaBIFN1 | AFA | 48 | 25 |
| pBaBIFN1 | AFA | 72 | 156 |
| pKPIFN | cgt | 24 | 4 |
| pKPIFN | cgt | 48 | 21 |
| pKPIFN | cgt | 72 | 95 |
| pKP651 | phoA | 24 | 0 |
| pKP651 | phoA | 48 | 0 |
| pKP651 | phoA | 72 | 22 |
| pKP652 | ompA | 24 | 4 |
| pKP652 | ompA | 48 | 18 |
| pKP652 | ompA | 72 | 41 |

This result shows unambiguously that the signal sequence according to the invention SEQ ID NO: 2 is superior to the other signal sequences as regards the yield and secretion of the protein to be produced.

Example 3: Creation of an Improved CGTAse Production Plasmid by the Insertion of the Signal Sequence According to the Invention The plasmid pCGT (see Example 1) bears the gene for a CGTase in-frame fused to the signal sequence for the CGTase. This signal sequence was now replaced by the signal sequence according to the invention.

For this, the 8448 bp plasmid was cleaved with the restriction enzymes SspI and BglII in a partial digestion by methods known to the person skilled in the art. The 8119 bp fragment was isolated and treated with Klenow enzyme, whereby the ends were smoothed. The 329 bp fragment, which contains the CGTase signal sequence and about 150 bp of the 5' end of the CGTase gene, was removed.

The following 329 bp DNA fragment, which is identical to the aforesaid fragment as regards sequence, except that the CGTase signal sequence has been replaced by the signal sequence according to the invention, was prepared by gene synthesis:

SEQ ID NO: 11

ATTCTGAAATGAGCTGTTGACAATTAATCATCGGCTCGTATAATGTGTGG

AATTGTGAGCGGATAACAATTTCACACAGGAAACAGATAATGAAAAGAAA

CCGTTTTTTTAATACCTCGGCTGCTATTGCCATTTCGATTGCATTACAGA

TCTTTTTTCCGTCCGCTTCCGCTTTCGCTGCTGAACCAGAAGAAACTTAT

CTTGATTTTCGTAAGGAGACAGATATATTTTCTATTCCTTGATCGTTTCA

GCGATGGAGATCCAAGTAATAATGCAGGGTTTAATTCTGCAACCTACGAT

CCTAATAATTTAAAAAAATATACTGGAGGA

This DNA fragment was ligated with the 8119 bp fragment isolated, by a method known to the person skilled in the art. The plasmid pCM703AFA formed in this manner was checked by sequencing.

Example 4: Improvement of CGTase Production by Use of the Signal Sequence According to the Invention Plasmid pCM703AFA and plasmid pCGT (see Example 3) were introduced into the following strains by transformation by standard methods (e.g. by $CaCl_2$ transformation):

K802=CGSC* 5610: Yang et al., 1998

WCM105: preparable according to EP0338410B1

Selection for plasmid-containing strains was effected using ampicillin (100 mg/L).

As a result, the following strains according to the invention were obtained:

WCM105/pCM703AFA

K802/pCM703AFA

And the following control strains:

WCM105/pCGT

K802/pCGT

These strains were used for the production of a cyclodextrin-glycosyltransferase and are grown in 10 ml in LB medium with 1% glucose and 100 mg/L ampicillin at 30° C. At OD 0.5, the production of the cyclodextrin glycosyltransferase is induced by addition of IPTG (isopropylthiogalactoside) to 0.5 mM. In the supernatant of the cultures of the strains, the yield of cyclodextrin glycosyltransferase was determined by the following activity test:

Test buffer: 5 mM Tris-HCl buffer>pH 6.5, 5 mM $CaSO_4.2H_2O$

Substrate: 10% Noredux solution in test buffer (pH 6.5)

Test preparation: 1 ml substrate solution+1 ml centrifuged culture supernatant (5 mins, 12,000 rpm)+3 ml methanol Reaction temperature: 40° C.

Enzyme Test:

Preconditioning of the solutions (ca. 5 mins at 40° C.)

Addition of the enzyme solution to the substrate solution; rapid mixing (Whirl mixer)

Incubation for 3 mins at 40° C.

Stopping of the enzyme reaction by addition of methanol; rapid mixing (Whirl mixer)

Cooling of the mixture on ice (ca. 5 mins)

Centrifuging down (5 mins, 12,000 rpm) and pipetting off the clear supernatant

HPLC analysis of the CD produced

Enzyme activity: A=G*V1*V2/(t*MG) (units/ml)

A=activity

G=Content of CD in mg/l =test mixture: area units×$10^4$/ Standard solution (10 mg/ml)/area units V1=dilution factor/test mixture (→5)

V2=dilution factor/enzyme solution t=reaction time in mins (→3)

MG=molecular weight in g/mol (CD→973)

1 Unit=1•Mol product/min.

TABLE 2

Yield of cyclodextrin glycosyltransferase in various strains.

| Strain | cyclodextrin glycosyltransferase produced (U/ml) |
|---|---|
| WCM105/pCGT | 99 |
| WCM105/pCM703AFA | 158 |
| K802/pCGT | 67 |
| K802/pCM703AFA | 81 |

Example 5: Improvement of Hirudin Production by Use of the Signal Sequence According to the Invention The plasmid pCMT203 described in patent EP0448093B1 was altered by replacement of the signal sequence used by the signal sequence according to the invention AFA. This replacement was effected analogously to Examples 1 and 3. The plasmid formed was named pCMT203AFA.

pCMT203 and pCMT203AFA were introduced into strain WCM105 (preparable according to EP0338410B1) by transformation by standard methods (e.g. by $CaCl_2$ transformation).

Selection for plasmid-containing strains was effected using ampicillin (100 mg/L).

The following strains were obtained:

WCM105/pCMT203

WCM105/pCMT203AFA

Both strains were cultured in a 10 l fermenter, as described in EP0448093B1, and the hirudin formed was quantified, as described in EP0448093B1, 45 hrs after addition of IPTG. The results in Table 3 show that the use of the signal sequence according to the invention leads to increased yields of hirudin.

TABLE 3

Yield of hirudin (in AT-U/ml and g/L) in 10 l fermentations 45 hrs after induction with IPTG in various strains.

| Strain | Hirudin (AT-U/ml) | Hirudin (g/L) |
|---|---|---|
| WCM105/pCMT203 | 42000 | 2.63 |
| WCM105/pCMT203AFA | 55400 | 3.47 |

Example 6: Improvement of the Production of a Functional Fab Antibody Fragment by Use of the Signal Sequence According to the Invention The present example describes the improved production of a Fab fragment of the well-characterized anti-lysozyme antibody D1.3.

As the starting vector for the cloning and expression of the genes of the anti-lysozyme Fab fragment, the plasmid pJF118ut (see Example 1) was used. The two reading frames for the heavy chain ($V_H$-$C_H$1 domains) and for the light chain ($V_L$-$C_L$ domains) of the anti-lysozyme Fab fragment each including a signal sequence were cloned into this plasmid in two consecutive steps.

For this, the following procedure was used: The DNA fragment with the SEQ ID NO: 12 (heavy chain) was prepared by gene synthesis and contains a gene fusion product consisting of the signal sequence of the ompA gene of *E. coli* and the reading frame for the heavy chain ($V_H$-$C_H$1) of the Fab fragment. Six histidine codons directly follow this reading frame and thus form the C terminus of the fusion protein. By means of this His tag, a simple purification of the fully assembled Fab fragment is subsequently possible by affinity chromatography. This DNA fragment was cleaved with the restriction enzymes EcoRI and PstI and ligated with the expression vector pJF118ut, which had been cleaved with the same restriction enzymes. The plasmid resulting from this cloning, wherein the expression of the gene for the heavy chain is under the control of the tac promoter, was described as pHC-anti-lysozyme.

The DNA fragment with the SEQ ID NO: 13 (light chain) was also prepared by gene synthesis and contains a gene fusion product consisting of a DNA sequence coding for the signal peptide of a CGTase described in SEQ ID NO: 3 (shown bold in SEQ ID NO: 7) and the reading frame for the light chain ($V_L$-$C_L$) of the Fab fragment. This DNA fragment was first cleaved with the restriction enzyme PstI and then ligated with the vector pHC-anti-lysozyme, which had been cleaved with the same restriction enzyme. The plasmid resulting from this was described as pFab-anti-lysozyme (FIG. 9). In this manner, an artificial operon consisting of the respective reading frames for the heavy and the light chain, which is under the control of the tac promoter, was created. With this, synchronous expression of both genes is possible by addition of an inducer (e.g. IPTG).

For the preparation of the plasmids according to the invention pFab-anti-lysozymeVLAFA and pFab-anti-lysozymeVHAFA, either the signal sequence for the light chain (pFab-anti-lysozymeVLAFA) or the signal sequence for the heavy chain (pFab-anti-lysozymeVHAFA) was replaced with the signal sequence according to the invention SEQ ID NO: 2 in a manner analogous to that described in Example 1.

For the preparation of the anti-lysozyme-Fab fragment, the strain WCM105 (see Example 4) was transformed by the $CaCl_2$ method with the plasmids pFab-anti-lysozyme and pFab-anti-lysozymeVLAFA or pFab-anti-lysozymeVHAFA. The selection for plasmid-containing cells was effected using ampicillin (100 mg/l).

The production of the anti-lysozyme-Fab fragment was carried out on the 10 l scale. The production process was carried out in 10 l stirred tank fermenters.

The fermenter filled with 6 l of the medium FM4 (1.5 g/l $KH_2PO_4$, 5 g/l $(NH_4)_2SO_4$, 0.3 g/l $MgSO_4\times7H_2O$, 0.05 g/l $CaCl_2\times2H_2O$, 0.075 g/l $FeSO_4\times7H_2O$, 1 g/l $Na_3$citrate$\times2H_2O$, 0.5 g/l NaCl), 1 ml/l trace element solution (0.15 g/l $Na_2MoO_4\times2H_2O$, 2.5 g/l $Na_3BO_3$, 0.7 g/l $CoCl_2\times6H_2O$, 0.25 g/l $CuSO_4\times5H_2O$, 1.6 g/l $MnCl_2\times4H_2O$, 0.3 g/l $ZnSO_4\times7H_2O$), 5 mg/l vitamin $B_1$, 3 g/l phytone, 1.5 g/l yeast extract, 10 g/l glucose, 100 mg/l ampicillin was inoculated in the ratio 1:10 with a preculture which had been cultured overnight in the same medium. During the fermentation, a temperature of 30° C. was set and the pH value was kept constant at a value of 7.0 by metering in $NH_4OH$ or $H_3PO_4$. Glucose was metered in throughout the fermentation so that the maximal glucose concentration in the medium was <10 g/l. Expression was induced by addition of isopropyl-β-D-thiogalactopyranoside (IPTG) to 0.1 mM at the end of the logarithmic growth phase.

After 72 hrs fermentation, samples were taken, and the cells removed from the culture medium by centrifugation. The anti-lysozyme-Fab fragment was purified from the culture supernatants by affinity chromatography, as described in Skerra (1994, Gene 141, 79-84).

The quantification and determination of the activity of the purified anti-lysozyme-Fab fragment were performed by means of an ELISA test with lysozyme as the antigen (Skerra, 1994, Gene 141, 79-84).

In Table 4, the yields of functional anti-lysozyme-Fab fragment that could be isolated in each case from 20 ml of culture supernatant after 72 hrs fermentation are listed.

TABLE 4

Anti-lysozyme-Fab fragment yields in the culture supernatant after 72 hrs fermentation

| Strain | Anti-lysozyme-Fab fragment [mg] purified from 20 ml of supernatant | anti-lysozyme-Fab fragment yield [g/l] in the culture supernatant (extrapolated) |
|---|---|---|
| WCM105/ pFab-anti-lysozyme | 25 | 1.25 |
| WCM105/ pFab-anti-lysozymeVLAFA | 30 | 1.5 |
| WCM105/ pFab-anti-lysozymeVHAFA | 33 | 1.65 |

What is claimed is:

1. An isolated signal peptide with a cleavage site to a recombinant protein, wherein the last three amino acids before the cleavage site are alanine-phenylalanine-alanine (AFA), the signal peptide comprising SEQ ID NO: 1.

2. An isolated signal peptide with a cleavage site to a recombinant protein the amino acid sequence of which comprises SEQ ID NO: 1 but with 1 to 3 conservative amino acid substitutions, wherein the last three amino acids before the cleavage site are alanine-phenylalanine-alanine (AFA).

3. An isolated signal peptide with a cleavage site to a recombinant protein the amino acid sequence of which comprises SEQ ID NO: 1 but with 1 conservative amino acid substitution, wherein the last three amino acids before the cleavage site are alanine-phenylalanine-alanine (AFA).

* * * * *

SEQUENCE LISTING

```
<160> NUMBER OF SEQ ID NOS: 13

<210> SEQ ID NO 1
<211> LENGTH: 30
<212> TYPE: PRT
<213> ORGANISM: Artificial Sequence
<220> FEATURE:
<223> OTHER INFORMATION: Amino acid sequence of the "AFA" signal peptide

<400> SEQUENCE: 1
```

```
Met Lys Arg Asn Arg Phe Phe Asn Thr Ser Ala Ala Ile Ala Ile Ser
1               5                   10                  15

Ile Ala Leu Gln Ile Phe Phe Pro Ser Ala Ser Ala Phe Ala
            20                  25                  30


<210> SEQ ID NO 2
<211> LENGTH: 90
<212> TYPE: DNA
<213> ORGANISM: Artificial Sequence
<220> FEATURE:
<223> OTHER INFORMATION: DNA sequence of the "AFA" signal peptide

<400> SEQUENCE: 2

atgaaaagaa accgtttttt taatacctcg gctgctattg ccatttcgat tgcattacag     60

atctttttc cgtccgcttc cgctttcgct                                       90


<210> SEQ ID NO 3
<211> LENGTH: 30
<212> TYPE: PRT
<213> ORGANISM: Klebsiella spec.
<220> FEATURE:
<221> NAME/KEY: MISC_FEATURE
<223> OTHER INFORMATION: Amino acid sequence of the "cgt" signal peptide

<400> SEQUENCE: 3

Met Lys Arg Asn Arg Phe Phe Asn Thr Ser Ala Ala Ile Ala Ile Ser
1               5                   10                  15

Ile Ala Leu Asn Thr Phe Phe Cys Ser Met Gln Thr Ile Ala
            20                  25                  30


<210> SEQ ID NO 4
<211> LENGTH: 2065
<212> TYPE: DNA
<213> ORGANISM: Artificial Sequence
<220> FEATURE:
<223> OTHER INFORMATION: DNA molecule which contains the CGTase gene
      from Klebsiella pneumoniae
<220> FEATURE:
<221> NAME/KEY: sig_peptide
<222> LOCATION: (4)..(93)
<223> OTHER INFORMATION: signal sequence of the CGTase gene
<220> FEATURE:
<221> NAME/KEY: allele
<222> LOCATION: (94)..(1971)
<223> OTHER INFORMATION: structural gene of the CGTase gene

<400> SEQUENCE: 4

ataatgaaaa gaaaccgttt ttttaatacc tcggctgcta ttgccatttc gattgcatta     60

aatacttttt tttgtagcat gcagacgatt gctgctgaac cagaagaaac ttatcttgat    120

tttcgtaagg agacgatata ttttctattc cttgatcgtt tcagcgatgg agatccaagt    180

aataatgcag ggtttaattc tgcaacctac gatcctaata atttaaaaaa atatactgga    240

ggagatctcc gggggttgat taataaacta ccctatttaa aatcacttgg tgttacttca    300

atctggatta ctcccccaat cgataatgtg aataatactg atgctgctgg caatactgga    360

tatcatggtt attggggaag agattatttt cgtatagatg aacattttgg caatctcgat    420

gatttcaaag aactgactag tttgatgcat agtcctgatt ataatatgaa actggttctt    480

gattatgccc ctaatcattc gaatgctaat gatgaaaatg aatttggtgc actatatcgt    540

gatggtgtgt ttattactga ttatcctacg aatgttgccg ccaatacggg ctggtatcat    600

cacaatggtg gggtaacgaa ctggaatgat ttcttccaag tgaagaatca taatctattc    660

aatctatcag acctcaatca atccaatact gatgtctacc agtacttgtt ggatggttct    720
```

```
aaattttgga tcgatgctgg tgtggatgct atcaggattg atgccatcaa gcatatggac    780

aagtctttta tacagaaatg gaccagcgat atttatgatt acagtaagtc tatcggccgg    840

gaaggatttt ttttcttcgg tgaatggttt ggtgccagtg cgaatactac aacaggtgtt    900

gatggtaatg ctatcgatta cgccaacact tccgggtcag cgttgctgga ttttggattc    960

cgcgatactt tagaaagagt tttggtagga cgtagcggaa atacaatgaa aacgttaaat   1020

agttatctga taaaaagaca aacagtcttt accagtgatg actggcaggt tgtttttatg   1080

gataaccatg atatggcacg cattggtacc gctctgcgtt caaacgccac tacttttggt   1140

cctggaaata atgaaaccgg tggaagtcag agtgaagctt ttgctcagaa acgtatagac   1200

ctcggtctgg ttgcgacaat gactgtacgt ggtattcctg ccatttatta tggtactgaa   1260

cattatgccg ctaactttac ctctaacagt tttggtcaag ttggcagtga tccttacaac   1320

cgagagaaaa tgccaggatt tgatacggaa agtgaggctt tctccattat taaaacactg   1380

ggtgacctaa ggaaaagtag cccggcaatt caaaatggaa cttatactga actatgggtt   1440

aatgatgata tattagtatt tgagcggcgt tctgggaacg atattgttat tgttgcactt   1500

aatcgtggtg aggctaacac aattaatgtt aaaaatatag cggttcctaa tggggtatat   1560

ccgagtttga ttgggaataa tagtgtttca gtagcaaata aacggacaac actaacactt   1620

atgcaaaatg aagctgttgt cattcgctca caatcagatg atgcggagaa ccctacagta   1680

caaagcataa acttcacatg taataacggt tatacgattt caggtcaaag tgtttatatt   1740

attggtaata tacctcagtt aggtggttgg gacttaacta aagcggtaaa aatatcaccg   1800

acacaatatc cacaatggag tgcgagctta gagcttcctt ctgacttaaa tgttgaatgg   1860

aagtgtgtga aacgtaatga aaccaatccg acggctaatg ttgagtggca gtctggtgca   1920

aataaccagt tcaatagcaa tgacacacaa acaacgaatg gctcgtttta attaaaattt   1980

agtggaccag cgttccaatc gatggtccac tattcgtact ccggccataa ttatttttga   2040

ctaatactct tacaaatttt caacc                                         2065
```

```
<210> SEQ ID NO 5
<211> LENGTH: 700
<212> TYPE: DNA
<213> ORGANISM: Artificial Sequence
<220> FEATURE:
<223> OTHER INFORMATION: DNA sequence of a phoA-IFNalpha2b gene fusion
      product

<400> SEQUENCE: 5

attctgaaat gagctgttga caattaatca tcggctcgta taatgtgtgg aattgtgagc     60

ggataacaat ttcacacagg aaacagaatt ctaaggagga aattatatga aacaaagcac    120

tattgcactg gcactcttac cgttactgtt tacccctgtg acaaaagctt gtgacttacc    180

tcagacccat tcactgggct cacgccgtac gctgatgctg ttagcacaga tgcgtcgcat    240

ttctctgttt agttgtttga aagaccgtca tgattttggg ttcccgcaag aagagtttgg    300

taatcagttt cagaaagccg aaactattcc ggttctgcac gaaatgattc aacagatttt    360

taacctgttt tcgacaaagg atagctctgc cgcgtgggat gaaaccttac tggataagtt    420

ctacaccgaa ctgtaccagc aactgaatga tctggaagca tgcgttatcc agggcgtggg    480

tgtcacagaa actccgctga tgaaggagga cagcattctg gcggtgcgca aatatttcca    540

gcgtatcacg ctgtatctga aagagaaaaa atattcgcca tgcgcgtggg aggtcgtgcg    600

cgcggagatc atgcgcagtt tctctttgag caccaacctg caagaatcct tgcgttccaa    660
```

-continued

```
agaataatag tctagaagct tggctgtttt ggcggatgag                            700


<210> SEQ ID NO 6
<211> LENGTH: 700
<212> TYPE: DNA
<213> ORGANISM: Artificial Sequence
<220> FEATURE:
<223> OTHER INFORMATION: DNA sequence of a ompA-IFNalpha2b gene fusion
      product

<400> SEQUENCE: 6

attctgaaat gagctgttga caattaatca tcggctcgta taatgtgtgg aattgtgagc      60

ggataacaat ttcacacagg aaacagaatt ctaaggagga aattatatga aaaagacagc     120

tatcgcgatt gcagtggcac tggctggttt cgctaccgta gcgcaggctt gtgacttacc     180

tcagacccat tcactgggct cacgccgtac gctgatgctg ttagcacaga tgcgtcgcat     240

ttctctgttt agttgtttga aagaccgtca tgattttggg ttcccgcaag aagagtttgg     300

taatcagttt cagaaagccg aaactattcc ggttctgcac gaaatgattc aacagatttt     360

taacctgttt tcgacaaagg atagctctgc cgcgtgggat gaaaccttac tggataagtt     420

ctacaccgaa ctgtaccagc aactgaatga tctggaagca tgcgttatcc agggcgtggg     480

tgtcacagaa actccgctga tgaaggagga cagcattctg gcggtgcgca aatatttcca     540

gcgtatcacg ctgtatctga aagagaaaaa atattcgcca tgcgcgtggg aggtcgtgcg     600

cgcggagatc atgcgcagtt tctctttgag caccaacctg caagaatcct tgcgttccaa     660

agaataatag tctagaagct tggctgtttt ggcggatgag                            700


<210> SEQ ID NO 7
<211> LENGTH: 727
<212> TYPE: DNA
<213> ORGANISM: Artificial Sequence
<220> FEATURE:
<223> OTHER INFORMATION: DNA sequence of a cgt-IFNalpha2b gene fusion
      product

<400> SEQUENCE: 7

attctgaaat gagctgttga caattaatca tcggctcgta taatgtgtgg aattgtgagc      60

ggataacaat ttcacacagg aaacagaatt ctaaggagga aattatatga aaagaaaccg     120

ttttttaat acctcggctg ctattgccat ttcgattgca ttaaatactt ttttttgtag     180

catgcagacg attgcttgtg acttacctca gacccattca ctgggctcac gccgtacgct     240

gatgctgtta gcacagatgc gtcgcatttc tctgtttagt tgtttgaaag accgtcatga     300

ttttgggttc ccgcaagaag agtttggtaa tcagtttcag aaagccgaaa ctattccggt     360

tctgcacgaa atgattcaac agatttttaa cctgttttcg acaaaggata gctctgccgc     420

gtgggatgaa accttactgg ataagttcta caccgaactg taccagcaac tgaatgatct     480

ggaagcatgc gttatccagg gcgtgggtgt cacagaaact ccgctgatga aggaggacag     540

cattctggcg gtgcgcaaat atttccagcg tatcacgctg tatctgaaag agaaaaaata     600

ttcgccatgc gcgtgggagg tcgtgcgcgc ggagatcatg cgcagtttct ctttgagcac     660

caacctgcaa gaatccttgc gttccaaaga ataatagtct agaagcttgg ctgttttggc     720

ggatgag                                                                727


<210> SEQ ID NO 8
<211> LENGTH: 727
<212> TYPE: DNA
<213> ORGANISM: Artificial Sequence
<220> FEATURE:
```

<223> OTHER INFORMATION: DNA sequence of an AFA-IFNalpha2b gene fusion product

<400> SEQUENCE: 8

```
attctgaaat gagctgttga caattaatca tcggctcgta taatgtgtgg aattgtgagc     60

ggataacaat ttcacacagg aaacagaatt ctaaggagga aattatatga aaagaaaccg    120

ttttttaat acctcggctg ctattgccat ttcgattgca ttacagatct tttttccgtc    180

cgcttccgct ttcgcttgtg acttacctca gacccattca ctgggctcac gccgtacgct    240

gatgctgtta gcacagatgc gtcgcatttc tctgtttagt tgtttgaaag accgtcatga    300

ttttgggttc ccgcaagaag agtttggtaa tcagtttcag aaagccgaaa ctattccggt    360

tctgcacgaa atgattcaac agatttttaa cctgttttcg acaaaggata gctctgccgc    420

gtgggatgaa accttactgg ataagttcta caccgaactg taccagcaac tgaatgatct    480

ggaagcatgc gttatccagg gcgtgggtgt cacagaaact ccgctgatga aggaggacag    540

cattctggcg gtgcgcaaat atttccagcg tatcacgctg tatctgaaag agaaaaaata    600

ttcgccatgc gcgtgggagg tcgtgcgcgc ggagatcatg cgcagtttct ctttgagcac    660

caacctgcaa gaatccttgc gttccaaaga ataatagtct agaagcttgg ctgttttggc    720

ggatgag                                                              727
```

<210> SEQ ID NO 9
<211> LENGTH: 21
<212> TYPE: PRT
<213> ORGANISM: Escherichia coli
<220> FEATURE:
<221> NAME/KEY: MISC_FEATURE
<223> OTHER INFORMATION: Amino acid sequence of the phoA signal peptide of Escherichia coli

<400> SEQUENCE: 9

```
Met Lys Gln Ser Thr Ile Ala Leu Ala Leu Leu Pro Leu Leu Phe Thr
1               5                   10                  15

Pro Val Thr Lys Ala
            20
```

<210> SEQ ID NO 10
<211> LENGTH: 21
<212> TYPE: PRT
<213> ORGANISM: Escherichia coli
<220> FEATURE:
<221> NAME/KEY: MISC_FEATURE
<223> OTHER INFORMATION: Amino acid sequence of the ompA signal peptide of Escherichia coli

<400> SEQUENCE: 10

```
Met Lys Lys Thr Ala Ile Ala Ile Ala Val Ala Leu Ala Gly Phe Ala
1               5                   10                  15

Thr Val Ala Gln Ala
            20
```

<210> SEQ ID NO 11
<211> LENGTH: 329
<212> TYPE: DNA
<213> ORGANISM: Artificial Sequence
<220> FEATURE:
<223> OTHER INFORMATION: artificial DNA fragment which contains the sequence of the AFA signal peptide

<400> SEQUENCE: 11

```
attctgaaat gagctgttga caattaatca tcggctcgta taatgtgtgg aattgtgagc     60
```

```
ggataacaat ttcacacagg aaacagataa tgaaaagaaa ccgttttttt aatacctcgg    120

ctgctattgc catttcgatt gcattacaga tctttttttcc gtccgcttcc gctttcgctg    180

ctgaaccaga agaaacttat cttgattttc gtaaggagac gatatatttt ctattccttg    240

atcgtttcag cgatggagat ccaagtaata atgcagggtt taattctgca acctacgatc    300

ctaataattt aaaaaaatat actggagga                                      329
```

<210> SEQ ID NO 12
<211> LENGTH: 769
<212> TYPE: DNA
<213> ORGANISM: Artificial Sequence
<220> FEATURE:
<223> OTHER INFORMATION: DNA molecule which contains the gene of the heavy chain of the anti-lysozyme-Fab fragment
<220> FEATURE:
<221> NAME/KEY: sig_peptide
<222> LOCATION: (24)..(86)
<223> OTHER INFORMATION: ompA signal peptide
<220> FEATURE:
<221> NAME/KEY: allele
<222> LOCATION: (87)..(758)
<223> OTHER INFORMATION: Gene of the heavy chain of the anti-lysozyme Fab fragment incl. His tag (bp 738-755)

<400> SEQUENCE: 12

```
cagaattcta aggaggaaat tatatgaaaa agacagctat cgcgattgca gtggcactgg     60

ctggtttcgc taccgtagcg caggctgaag ttaaactgca agaatccggt ccgggtctgg    120

ttgctccgtc ccagtccctg tccatcacct gcaccgtttc cggtttctcc ctgaccggtt    180

acggtgttaa ctgggttcgt cagccgccgg gtaaaggtct ggaatggctg ggtatgatct    240

ggggtgacgg taacaccgac tacaactccg ctctgaaatc ccgtctgtcc atctccaaag    300

acaactccaa atcccaggtt ttcctgaaaa tgaactccct gcacaccgac gacaccgctc    360

gttactactg cgctcgtgaa cgtgactacc gtctggacta ctggggtcag ggtaccaccg    420

ttaccgtttc ctccgctaaa accaccccgc cgtccgttta cccgctggct ccgggttccg    480

ctgctcagac caactctatg gttaccctgg gttgcctggt taaaggttac ttcccggaac    540

cggttaccgt tacctggaac tccggttccc tgtcctccgg ttgccacacc ttcccggctg    600

ttctgcaatc cgacctgtac accctgtcct cctccgttac cgttccgtcc tccacctggc    660

cgtccgaaac cgttacctgc aacgttgctc acccggcttc ctccaccaaa gttgacaaaa    720

aaatcgttcc gcgtgaccat caccaccatc accattaata actgcagaa                769
```

<210> SEQ ID NO 13
<211> LENGTH: 768
<212> TYPE: DNA
<213> ORGANISM: Artificial Sequence
<220> FEATURE:
<223> OTHER INFORMATION: DNA molecule which contains the gene of the light chain of the anti-lysozyme Fab fragment
<220> FEATURE:
<221> NAME/KEY: sig_peptide
<222> LOCATION: (26)..(115)
<223> OTHER INFORMATION: CGTase-Signal Sequence
<220> FEATURE:
<221> NAME/KEY: allele
<222> LOCATION: (116)..(757)
<223> OTHER INFORMATION: gene of the light chain of the anti-lysozyme Fab fragment

<400> SEQUENCE: 13

```
aactgcagta catggagaaa ataaaatgaa aagaaaccgt tttttaata cctcggctgc     60

tattgccatt tcgattgcat taaatacttt tttttgtagc atgcagacga ttgctgacat    120
```

-continued

```
cgaactgacc cagtccccgg cttccctgtc cgcttccgtt ggtgaaaccg ttaccatcac    180

ctgccgtgct tccggtaaca tccacaacta cctggcttgg taccagcaga aacagggtaa    240

atccccgcag ctgctggttt actacaccac caccctggct gacggtgttc cgtcccgttt    300

ctccggttcc ggttccggta cccagtactc cctgaaaatc aactccctgc aaccggaaga    360

cttcggttcc tactactgcc agcacttctg gtccaccccg cgtaccttcg gtggtggtac    420

caaactggaa ctgaaacgtg ctgacgctgc tccgaccgtt tccatcttcc cgccgtcctc    480

cgaacagctg acctccggtg gtgcttccgt tgtttgcttc ctgaacaact tctacccgaa    540

agacatcaac gttaaatgga aaatcgacgg ttccgaacgt cagaacggtg ttctgaactc    600

ctggaccgac caggactcca aagactccac ctactccatg tcctccaccc tgaccctgac    660

caaagacgaa tacgaacgtc acaactccta cacctgcgaa gctacccaca aaacctccac    720

ctccccgatc gttaaatcct tcaaccgtaa cgaataatag ctgcagaa                 768
```